US011830979B2

(12) United States Patent
Lee et al.

(10) Patent No.: US 11,830,979 B2
(45) Date of Patent: Nov. 28, 2023

(54) ELECTROLYTE FOR LITHIUM SECONDARY BATTERY AND LITHIUM SECONDARY BATTERY COMPRISING SAME

(71) Applicants: HYUNDAI MOTOR COMPANY, Seoul (KR); KIA CORPORATION, Seoul (KR); UNIST (ULSAN NATIONAL INSTITUTE OF SCIENCE AND TECHNOLOGY), Ulsan (KR)

(72) Inventors: Yoon Sung Lee, Suwon-si (KR); Ik Kyu Kim, Gwangmyeong-si (KR); Seung Min Oh, Incheon (KR); Sung Ho Ban, Hwaseong-si (KR); Sang Mok Park, Gwangju-si (KR); Ko Eun Kim, Cheongju-si (KR); Sang Kyu Kwak, Ulsan (KR); Nam Soon Choi, Ulsan (KR); Hyeon Gyu Moon, Ulsan (KR); Seo Young Jeong, Ulsan (KR); Sung You Hong, Ulsan (KR); Dae Yeon Hwang, Ulsan (KR)

(73) Assignees: HYUNDAI MOTOR COMPANY, Seoul (KR); KIA CORPORATION, Seoul (KR); UNIST (ULSAN NATIONAL INSTITUTE OF SCIENCE AND TECHNOLOGY), Ulsan (KR)

(*) Notice: Subject to any disclaimer, the term of this patent is extended or adjusted under 35 U.S.C. 154(b) by 196 days.

(21) Appl. No.: 17/339,328

(22) Filed: Jun. 4, 2021

(65) Prior Publication Data

US 2022/0115696 A1 Apr. 14, 2022

(30) Foreign Application Priority Data

Oct. 13, 2020 (KR) .......................... 10-2020-0132095

(51) Int. Cl.
 *H01M 10/0567* (2010.01)
 *H01M 10/0525* (2010.01)
 (Continued)

(52) U.S. Cl.
 CPC ....... *H01M 10/0567* (2013.01); *C07C 381/00* (2013.01); *C07F 5/04* (2013.01);
 (Continued)

(58) Field of Classification Search
 CPC ......... H01M 10/0567; H01M 10/0525; H01M 10/0568; H01M 10/0569; H01M 10/4235;
 (Continued)

(56) References Cited

U.S. PATENT DOCUMENTS

2022/0328878 A1* 10/2022 Sawa ................ H01M 10/0567

FOREIGN PATENT DOCUMENTS

CN 104752765 B 1/2017
CN 108091933 B 11/2019
 (Continued)

OTHER PUBLICATIONS

JPWO2016060038A1. Adeka Corporation. Apr. 21, 2016. English machine translation by EPO. (Year: 2016).*
 (Continued)

*Primary Examiner* — James Lee
(74) *Attorney, Agent, or Firm* — LEMPIA SUMMERFIELD KATZ LLC

(57) ABSTRACT

The electrolyte for a lithium secondary battery comprises: a lithium salt; a solvent; and a functional additive, wherein the functional additive comprises naphthalen-1-yl sulfurofluoridate, represented by the following formula 1:
 (Continued)

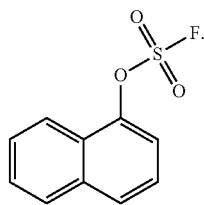

[Formula 1]

18 Claims, 3 Drawing Sheets

Figure 1:
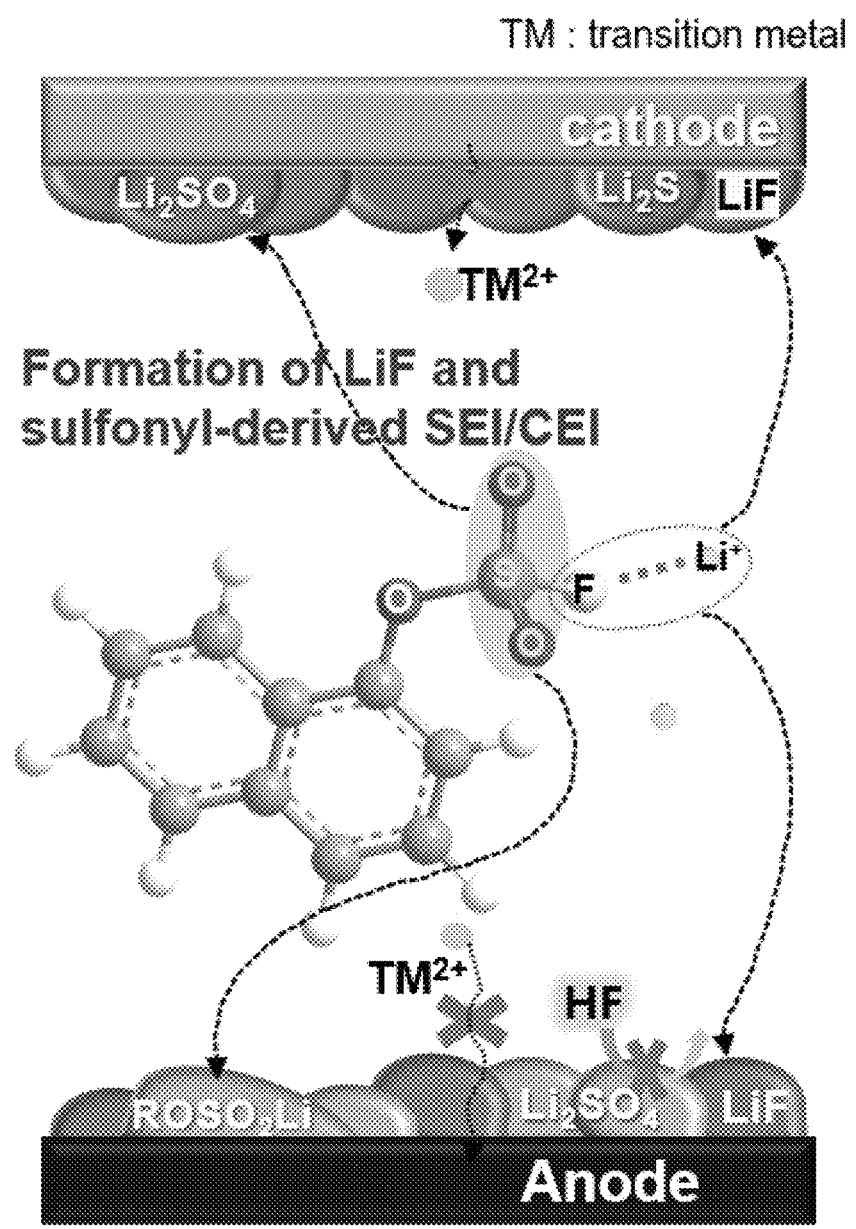

(51) Int. Cl.
*H01M 10/0568* (2010.01)
*C07C 381/00* (2006.01)
*C07F 5/04* (2006.01)
*H01M 4/38* (2006.01)
*H01M 4/505* (2010.01)
*H01M 4/525* (2010.01)
*H01M 4/587* (2010.01)
*H01M 10/0569* (2010.01)
*H01M 10/42* (2006.01)

(52) U.S. Cl.
CPC ........... *H01M 4/386* (2013.01); *H01M 4/505* (2013.01); *H01M 4/525* (2013.01); *H01M 4/587* (2013.01); *H01M 10/0525* (2013.01); *H01M 10/0568* (2013.01); *H01M 10/0569* (2013.01); *H01M 10/4235* (2013.01); *H01M 2300/0025* (2013.01)

(58) Field of Classification Search
CPC ...... H01M 4/386; H01M 4/505; H01M 4/525; H01M 4/587; H01M 2300/0025; C07C 381/00; C07C 5/04
See application file for complete search history.

(56) References Cited

FOREIGN PATENT DOCUMENTS

| | | |
|---|---|---|
| CN | 111129587 A | 5/2020 |
| KR | 10-2019-0092149 | 8/2019 |
| WO | 2016060038 A1 | 4/2016 |
| WO | WO 2020-009340 | 1/2020 |

OTHER PUBLICATIONS

Extended European Search Report issued in related Application No. EP 21177364.3 dated Nov. 25, 2021 (5 pages).

* cited by examiner

ELECTROLYTE FOR LITHIUM SECONDARY BATTERY AND LITHIUM SECONDARY BATTERY COMPRISING SAME

CROSS REFERENCE TO RELATED APPLICATION

The present application claims priority to and the benefit of Korean Patent Application No. 10-2020-0132095, filed on Oct. 13, 2020, the entire contents of which are incorporated herein by reference.

FIELD

The present disclosure relates to an electrolyte for a lithium secondary battery and a lithium secondary battery comprising the same.

BACKGROUND

The statements in this section merely provide background information related to the present disclosure and may not constitute prior art.

A lithium secondary battery is an energy storage system comprising a positive electrode for supplying lithium ions on charge, a negative electrode for receiving lithium ions, an electrolyte serving as a lithium ion transmission mediator, and a separator for separating the positive electrode and the negative electrode, wherein electric energy is generated and stored as chemical potentials change with intercalation/deintercalation in the positive and the negative electrode.

Such lithium secondary batteries have been used mainly in mobile electronic devices and are now rapidly expanding their use as an energy storage system to electric vehicles (EVs) and hybrid electric vehicles (HEVs) that have been successfully commercialized therewith.

In order to increase driving ranges of EVs, studies have been focused on the increase of energy density in lithium secondary batteries. An improvement of high capacity in the positive electrode makes it possible to increase an energy density in a lithium secondary battery.

Particularly, energy density in a battery depends greatly on characteristics of the positive and the negative electrode. Accordingly, a suitable electrolyte is desired for the electrodes to exhibit excellent electrochemical performance.

When a layered nickel (Ni)-rich $LiNi_{1-x-y}Co_xMn_yO_2$ (NCM; 1-x-y≥0.6) oxide is used as a high-capacity positive electrode active material, the capacity of the positive electrode can be increased by increasing the content of Ni or by raising a charge voltage. However, the charge/discharge performance rapidly degrades because the residual lithium components ($Li_2CO_3$ and LiOH) on the positive electrode promote degradation of the electrolyte and increase interfacial reactivity with the electrolyte, thus accelerating the degeneration rate.

Therefore, positive electrode-electrode and interface control techniques are very important.

The description given in the related art is only to understand the background of the present disclosure, but should not be recognized as a prior art already known to a person skilled in the art.

SUMMARY

The present disclosure provides an electrolyte for a lithium secondary battery, which can improve high-temperature lifetime characteristics in a lithium secondary battery, and a lithium secondary battery comprising the same.

An electrolyte for a lithium secondary battery according to one form of the present disclosure comprises a lithium salt, a solvent, and a functional additive, wherein the functional additive comprises naphthalen-1-yl sulfurofluoridate, represented by the following formula 1, as a first negative electrode film additive:

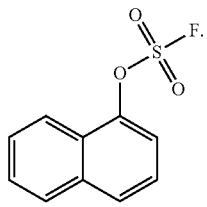

[Formula 1]

The first negative electrode film additive may be used in a total amount of 0.5-1.0 wt %, based on the weight of the electrolyte.

The functional additive may further comprise lithium difluoro(oxalato)borate, represented by the following formula 2, as a positive electrode film additive:

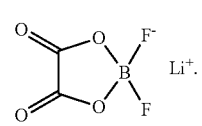

[Formula 2]

The positive electrode film additive may be used in an amount of 0.5-1.0 wt %, based on the total weight of the electrolyte.

The functional additive may further comprise vinylene carbonate (VC) as a second negative electrode film additive.

The second negative electrode film additive may be used in an amount of 0.5-3.0 wt %, based on the total weight of the electrolyte.

The lithium salt may be at least one compound selected from the group consisting of $LiPF_6$, $LiBF_4$, $LiClO_4$, LiCl, LiBr, LiI, $LiB_{10}Cl_{10}$, $LiCF_3SO_3$, $LiCF_3CO_2$, $LiAsF_6$, $LiSbF_6$, $LiAlCl_4$, $CH_3SO_3Li$, $CF_3SO_3Li$, $LiN(SO_2C_2F_5)_2$, $Li(CF_3SO_2)_2N$, $LiC_4F_9SO_3$, $LiB(C_6H_5)_4$, $Li(SO_2F)_2N$ (LiFSI), and $(CF_3SO_2)_2NLi$.

The solvent may be at least one substance selected from the group consisting of a carbonate-based solvent, an ester-based solvent, and a ketone-based solvent.

A lithium secondary battery according to one form of the present disclosure comprises the electrolyte described above. The lithium secondary battery may further comprise a positive electrode containing a positive electrode active material composed of Ni, Co, and Mn; a negative electrode containing at least one negative electrode active material selected from a carbon (C)-based material and silicon (Si)-based material; and a separator interposed between the positive electrode and the negative electrode.

The positive electrode may contain Ni at a content of 80 wt % or more.

Further areas of applicability will become apparent from the description provided herein. It should be understood that the description and specific examples are intended for purposes of illustration only and are not intended to limit the scope of the present disclosure.

DRAWINGS

Figure 2:
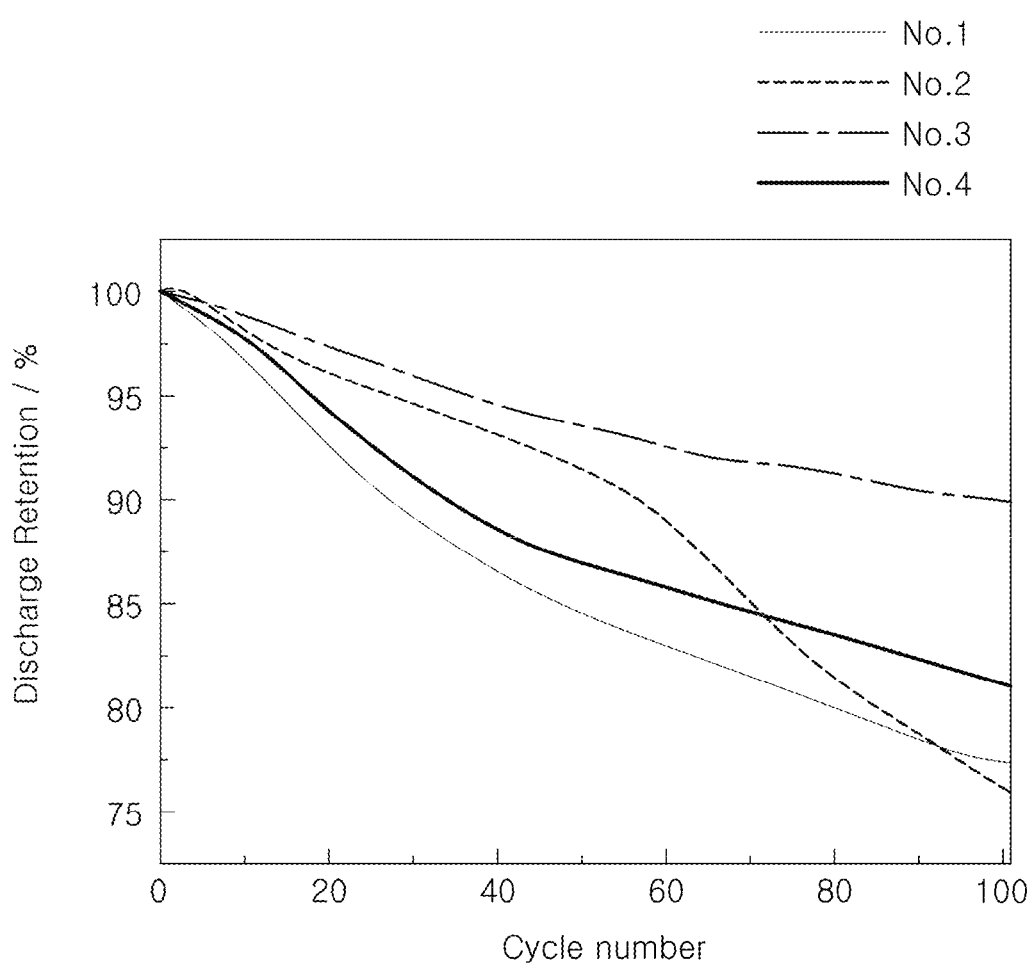
Figure 3:
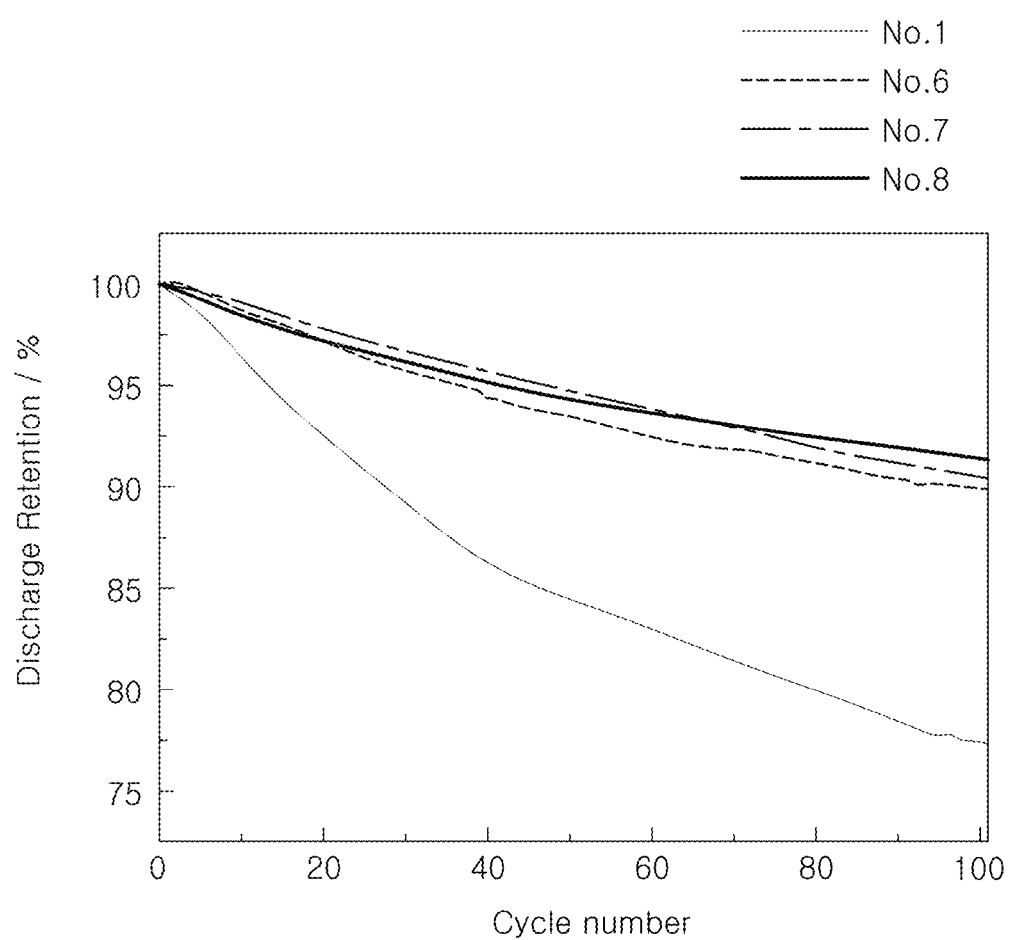

In order that the disclosure may be well understood, there will now be described various forms thereof, given by way of example, reference being made to the accompanying drawings, in which:

FIG. 1 is a view showing an event that occurs in an electrolyte to which the first negative electrode film additive and the positive electrode film additive according to one form of the present disclosure are added together; and FIGS. 2 and 3 are graphs showing charge/discharge test results in Examples and Comparative Examples, respectively.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

An electrolyte for a lithium secondary battery according to one form of the present disclosure comprises a lithium salt, a solvent, and a functional additive.

The lithium salt may be at least one compound selected from the group consisting of $LiPF_6$, $LiBF_4$, $LiClO_4$, LiCl, LiBr, LiI, $LiB_{10}Cl_{10}$, $LiCF_3SO_3$, $LiCF_3CO_2$, $LiAsF_6$, $LiSbF_F$, $LiAlCl_4$, $CH_3SO_3Li$, $CF_3SO_3Li$, $LiN(SO_2C_2F_5)_2$, $Li(CF_3SO_2)_2N$, $LiC_4F_9SO_3$, $LiB(C_6H_5)_4$, $Li(SO_2F)_2N$ (LiFSI), and $(CF_3SO_2)_2NLi$.

The lithium salt may exist at a total concentration of 0.1-1.2 moles in the electrolyte.

The solvent may be at least one substance selected from the group consisting of a carbonate-based solvent, an ester-based solvent, an ether-based solvent, and a ketone-based solvent.

In this regard, examples of the carbonate-based solvent include dimethyl carbonate (DMC), diethyl carbonate (DEC), dipropyl carbonate (DPC), methylpropyl carbonate (MPC), ethylpropyl carbonate (EPC), ethylmethyl carbonate (EMC), ethylene carbonate (EC), propylene carbonate (PC), butylene carbonate (BC), fluoroethylene carbonate (FEC), and vinylene carbonate (VC). The ester-based solvent may be exemplified by γ-butyrolactone (GBL), n-methyl acetate, n-ethyl acetate, n-propyl acetate, etc. As the ether-based solvent, dibutyl ether may be used, but without limitations thereto.

In addition, the solvent may further comprise an aromatic hydrocarbonate solvent. Examples of the aromatic carbohydrate solvent include benzene, fluorobenzene, bromobenzene, chlorobenzene, cyclohexyl benzene, isopropyl benzene, n-butylbenzene, octyl benzene, toluene, xylene, and mesitylene, which may be used alone or in combination.

The functional additive used in the electrolyte according to one form of the present disclosure may employ naphthalen-1-yl sulfurofluoridate (hereinafter referred to as "S3"), represented by the following formula 1, as a first negative electrode film additive

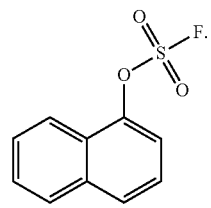

[Formula 1]

In this regard, naphthalen-1-yl sulfurofluoridate (S3), which serves as the first negative electrode film additive, stabilize the negative electrode by forming a film protective of the surface of the negative electrode material, and may be preferably added in an amount of 0.5-1.0 wt %, based on the total weight of the electrolyte.

When added in an amount less than 0.5 wt %, the first negative electrode film additive contributes only little effect because it cannot sufficiently form a surface protecting film on the surface of the negative electrode active material. More than 1.0 wt % of the first negative electrode film additive causes the excessive formation of a surface protecting layer, increasing a cell resistance, which results in a decreased lifetime.

Meanwhile, the functional additive may further comprise a positive electrode film additive functioning to form a film on a positive electrode active material. As the positive electrode film additive, lithium difluoro(oxalato)borate (hereinafter referred to as "LiFOB"), represented by following formula 2, may be used:

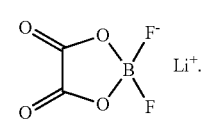

[Formula 2]

The positive electrode film additive, which is lithium difluoro(oxalato)borate (LiFOB), plays a role in stabilizing the positive electrode by forming a protecting film on the surface of the positive electrode active material. In addition, the positive electrode film additive inhibits the oxidative degradation of S3, which is the first negative electrode film additive, contributing to the formation of a film superb in thermal stability.

The positive electrode film additive may be preferably added in an amount of 0.5-1.0 wt %, based on the total weight of the electrolyte.

When added in an amount less than 0.5 wt %, the positive electrode film additive contributes only little effect because it cannot sufficiently form a surface protecting film on the surface of the positive electrode active material. More than 1.0 wt % of the positive electrode film additive causes the excessive formation of a surface protecting layer, increasing a cell resistance, which results in a decreased lifetime.

FIG. 1 is a view showing an event that occurs in an electrolyte to which the first negative electrode film additive and the positive electrode film additive according to one form of the present disclosure are added together.

The first negative electrode film additive S3 may be subjected to oxidative degradation on the positive electrode to produce sulfuric acid, with the resultant continuous degradation of the cell. However, as shown in FIG. 1, when added together with the first negative electrode film additive, the positive electrode film additive is decomposed on the surface of the positive electrode, prior to the first negative electrode film additive S3, to form stable CEI, thereby inhibiting the degradation of the cell.

Meanwhile, the functional additive may further comprise a second negative electrode film additive functioning to form a film on a negative electrode in addition to the first negative electrode film additive. For example, vinylene carbonate (hereinafter referred to "VC") may be used as the second negative electrode film additive.

The second negative electrode film additive may be preferably added in an amount of 0.5-3.0 wt %, based on the weight of the electrolyte. More preferably, the second negative electrode film additive may be added in an amount of 1.5-2.5 wt %.

Less than 0.5 wt % of the second negative electrode film additive reduces long-term lifetime characteristics of the cell. When exceeding 3.0 wt %, the amount of the second negative electrode film additive excessively forms a surface protecting layer causes increased cell resistance, resulting in a reduction in battery output.

According to one form thereof, the present disclosure provides a lithium secondary battery comprising the electrolyte described above, a positive electrode, a negative electrode, and a separator.

The positive electrode includes an NCM-based positive electrode active material composed of Ni, Co, and Mn. Particularly, the positive electrode active material in the positive electrode according to one form is composed only of an NCM-based positive electrode active material containing 80 wt % or more of Ni.

The negative electrode includes at least one substance selected from carbon (C)- and silicon (Si)-based negative electrode active materials.

The carbon (C)-based negative electrode active material may be at least one material selected from the group consisting of artificial graphite, natural graphite, graphitized carbon fibers, graphitized mesocarbon microbeads, fullerene, and amorphous carbon.

The silicon (Si)-based negative electrode active material may include a silicon oxide, a silicon particle, and a silicon alloy particle.

For the positive electrode and the negative electrode, the corresponding active material is mixed with a conductive material, a binder, and a solvent to prepare an electrode slurry. This electrode slurry is applied directly on a current collector and dried to manufacture the positive electrode or the negative electrode. In this regard, the current collector may be formed of aluminum (Al), but with no limitations thereto. Such electrode manufacturing methods are well known in the art and thus a detailed description is not given thereof.

The binder acts to well aggregate active material particles each other or strongly attach them to a current collector. Examples of the binder include, but are not limited to, polyvinyl alcohol, carboxymethyl cellulose, hydroxypropyl cellulose, diacetyl cellulose, polyvinyl chloride, carboxylated polyvinyl chloride, polyvinyl fluoride, ethylene oxide-bearing polymers, polyvinyl pyrrolidone, polyurethane, polytetrafluoroethylene, polyvinylidene fluoride, polyethylene, polypropylene, styrene butadiene rubber, acrylated styrene butadiene rubber, an epoxy resin, and nylon.

The conductive material is used to confer conductivity on the electrodes. So long as it is of electron conductivity without causing a chemical change in the battery, any conductive material is available. Examples of the conductive material include natural graphite, artificial graphite, carbon black, acetylene black, Ketjenblack, carbon fibers, and metal particles or fibers such as copper, nickel, aluminum, silver, etc. In addition, at least one conductive material such as a polyphenylene derivative may be further used.

The separator inhibits the formation of a short circuit between the positive electrode and the negative electrode while providing migration channels of lithium ions. This separator may well-known one, for example, a polyolefinic membrane such as polypropylene, polyethylene, polyethylene/polypropylene, polyethylene/polypropylene/polyethylene, polypropylene/polyethylene/polypropylene, etc., or a multiple membrane, microporous film, woven fabric, or non-woven fabric thereof. Alternatively, a porous polyolefin film coated with highly stable resin may be used.

Hereinafter, the present disclosure is explained with reference to Examples and Comparative Examples.

<Experiment 1> Test for Cell Resistance and High-Temperature Lifetime Characteristic at High Temperature (45° C.) According to Type and Amount of Functional Additive To examine cell resistance and high-temperature lifetime characteristics according to amounts and types of functional additives used in an electrolyte, a measurement was made of initial cell resistance and discharge retention after 100 cycles at a high temperature (45° C.) while types of functional additives were changed as shown in Table 1, below. The results are summarized in Table 1 and depicted in FIGS. 1 and 2.

In this regard, the cycles were performed under the conditions of cut-off: 2.7-4.35V, C-rate 1C, and temperature: 45° C. For preparing electrolytes, 0.5M $LiPF_6$+0.5 LiFSI was used as a lithium salt and a mixture of ethylene carbonate (EC):ethylmethyl carbonate (EMC):diethyl carbonate (DEC) at a volume ratio of 25:45:30.

The positive electrode was made of NCM811 while the negative electrode was a graphite electrode.

TABLE 1

| No. | | Additive | | | Initial cell resistance (%) | High temp. lifetime (%) @100 cyc |
|---|---|---|---|---|---|---|
| | VC | $LiPO_2F_2$ | S3 | LiFOB | | |
| 1 Comparative Example | 1.0 | — | — | — | 100 | 77.4 |
| 2 Comparative Example | — | — | 0.2 | — | 97 | 76.2 |
| 3 Example | — | — | 0.5 | — | 98 | 89.9 |
| 4 Example | — | — | 1.0 | — | 103 | 81.2 |
| 6 Comparative Example | 1.0 | 0.5 | — | — | 102 | 89.9 |
| 7 Example | 1.0 | — | 0.5 | — | 102 | 90.5 |
| 8 Example | 1.0 | — | 0.5 | 0.5 | 101 | 91.4 |

First, as shown in Table 1 and FIG. 2, an improvement in high-temperature lifetime was observed in Nos. 3 and 4 where the negative electrode film additive according to the present disclosure was added within the amount range suggested herein, compared to No. 1 where the typical functional additive VC was used.

Meanwhile, No. 2 to which the first negative electrode film additive according to the present disclosure was added in an amount less than the lower limit of the amount range suggested herein was inferior in terms of high-temperature lifetime compared to No. 1.

As can be understood from the data of Table 1 and FIG. 3, the high-temperature lifetime was further improved in No. 7, where the typical functional additive VC and the first negative electrode film additive according to the present disclosure were added, compared to No. 6, where the typical functional additive VC and the conventional negative electrode film additive LiPO$_2$F$_2$ were added in the same amounts.

Particularly, the highest improvement of high-temperature lifetime was detected in No. 8 where the typical functional additive VC was used together with a combination of the first negative electrode film additive and the positive electrode film additive.

As described hitherto, according to various forms of the present disclosure, the electrolyte can form CEI on the surface of a negative electrode active material to inhibit the degradation of the cell, thereby improving the lifetime of the lithium secondary battery.

Furthermore, the electrolyte guarantees lifetime stability at high temperatures and high voltages, contributing to an improvement of commercial value in the battery.

It will be appreciated by those having ordinary knowledge in the art to which the present disclosure pertains that the present disclosure may be practiced in other specific forms without changing the technical spirit and essential features of the present disclosure. Therefore, it should be understood that the above-described forms are illustrative but not restrictive in all aspects. The scope of the present disclosure is defined by the scope of the attached claims, rather than the detailed description. It should be appreciated that all variations and modifications derived from the scope of the claims and the equivalent concepts thereof are included in the scope of the present disclosure.

What is claimed is:

1. An electrolyte for a lithium secondary battery, the electrolyte comprising:
   a lithium salt;
   a solvent; and
   a functional additive,
   wherein the functional additive comprises naphthalen-1-yl sulfurofluoridate, represented by the following formula 1:

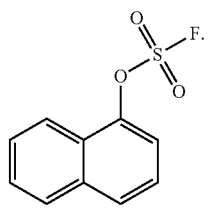

[Formula 1]

2. The electrolyte of claim 1, wherein the naphthalen-1-yl sulfurofluoridate is added in an amount of 0.5-1.0 wt %, based on a total weight of the electrolyte.

3. The electrolyte of claim 1, wherein the functional additive further comprises lithium difluoro(oxalato)borate, represented by the following formula 2:

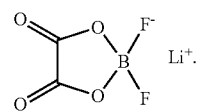

[Formula 2]

4. The electrolyte of claim 3, wherein the lithium difluoro(oxalato)borate is added in an amount of 0.5-1.0 wt %, based on a total weight of the electrolyte.

5. The electrolyte of claim 1, wherein the functional additive further comprises vinylene carbonate (VC).

6. The electrolyte of claim 5, wherein the vinylene carbonate (VC) is added in an amount of 0.5-3.0 wt %, based on a total weight of the electrolyte.

7. The electrolyte of claim 1, wherein the lithium salt is at least one compound selected from a group consisting of: LiPF$_6$, LiBF$_4$, LiClO$_4$, LiCl, LiBr, LiI, LiB$_{10}$Cl$_{10}$, LiCF$_3$SO$_3$, LiCF$_3$CO$_2$, LiAsF$_6$, LiSbF$_6$, LiAlCl$_4$, CH$_3$SO$_3$Li, CF$_3$SO$_3$Li, LiN(SO$_2$C$_2$F$_5$)$_2$, Li(CF$_3$SO$_2$)$_2$N, LiCF$_4$F$_9$SO$_3$, LiB(C$_6$Hs)$_4$, Li(SO$_2$F)$_2$N(LiFSI), and (CF$_3$SO$_2$)$_2$NLi.

8. The electrolyte of claim 1, wherein the solvent is at least one substance selected from a group consisting of: a carbonate-based solvent, an ester-based solvent, an ether-based solvent, and a ketone-based solvent.

9. A lithium secondary battery, comprising an electrolyte comprised of:
   a lithium salt;
   a solvent; and
   a functional additive, wherein the functional additive comprises naphthalen-1-yl sulfurofluoridate, represented by the following formula 1:

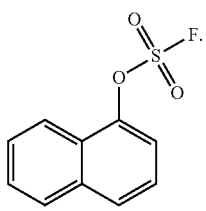

[Formula 1]

10. The lithium secondary battery of claim 9, further comprising:
    a positive electrode containing a positive electrode active material composed of Ni, Co, and Mn;
    a negative electrode containing at least one negative electrode active material selected from a carbon (C)-based material and silicon (Si)-based material; and
    a separator interposed between the positive electrode and the negative electrode.

11. The lithium secondary battery of claim 10, wherein the positive electrode contains Ni at a content of 80 wt % or more.

12. The lithium secondary battery of claim 9, wherein the naphthalen-1-yl sulfurofluoridate is added in an amount of 0.5-1.0 wt %, based on a total weight of the electrolyte.

13. The lithium secondary battery of claim 9, wherein the functional additive further comprises lithium difluoro(oxalato)borate, represented by the following formula 2:

[Formula 2]

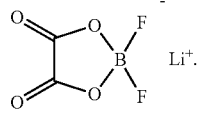

14. The lithium secondary battery of claim 13, wherein the lithium difluoro(oxalato)borate is added in an amount of 0.5-1.0 wt %, based on a total weight of the electrolyte.

15. The lithium secondary battery of claim 9, wherein the functional additive further comprises vinylene carbonate (VC).

16. The lithium secondary battery of claim 15, wherein the vinylene carbonate (VC) is added in an amount of 0.5-3.0 wt %, based on a total weight of the electrolyte.

17. The lithium secondary battery of claim 9, wherein the lithium salt is at least one compound selected from a group consisting of: $LiPF_6$, $LiBF_4$, $LiClO_4$, $LiCl$, $LiBr$, $LiI$, $LiB_{10}Cl_{10}$, $LiCF_3SO_3$, $LiCF_3CO_2$, $LiAsF_6$, $LiSbF_6$, $LiAlCl_4$, $CH_3SO_3Li$, $CF_3SO_3Li$, $LiN(SO_2C_2F_5)_2$, $Li(CF_3SO_2)_2N$, $LiCF_4F_9SO_3$, $LiB(C_6H_5)_4$, $Li(SO_2F)_2N$ (LiFSI), and $(CF_3SO_2)_2NLi$.

18. The lithium secondary battery of claim 9, wherein the solvent is at least one substance selected from a group consisting of: a carbonate-based solvent, an ester-based solvent, an ether-based solvent, and a ketone-based solvent.

\* \* \* \* \*